(12) United States Patent
Keady

(10) Patent No.: US 8,522,916 B2
(45) Date of Patent: *Sep. 3, 2013

(54) OCCLUSION EFFECT MITIGATION AND SOUND ISOLATION DEVICE FOR ORIFICE INSERTED SYSTEMS

(71) Applicant: Personics Holdings Inc., Boca Raton, FL (US)

(72) Inventor: Jon P. Keady, Fairfax Station, VA (US)

(73) Assignee: Personics Holdings Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,546

(22) Filed: Oct. 17, 2012

(65) Prior Publication Data

US 2013/0098706 A1  Apr. 25, 2013

Related U.S. Application Data

(63) Continuation of application No. 12/492,164, filed on Jun. 26, 2009, now Pat. No. 8,312,960.

(60) Provisional application No. 61/076,122, filed on Jun. 26, 2008.

(51) Int. Cl.
*A61B 7/02* (2006.01)
*H04R 25/00* (2006.01)

(52) U.S. Cl.
USPC .......................... 181/135; 381/322; 381/328

(58) Field of Classification Search
USPC .................... 181/135; 381/328, 322
See application file for complete search history.

(56) References Cited

U.S. PATENT DOCUMENTS

| | | | |
|---|---|---|---|
| 2,535,258 A | 12/1950 | Bland | |
| 3,602,654 A * | 8/1971 | Victoreen | 181/135 |
| 3,834,394 A * | 9/1974 | Hunter et al. | 606/195 |
| 4,133,984 A * | 1/1979 | Akiyama | 381/328 |
| 4,741,344 A | 5/1988 | Danby et al. | |
| 4,834,211 A | 5/1989 | Bibby et al. | |
| 4,896,679 A | 1/1990 | Pierre | |
| 4,962,537 A | 10/1990 | Basel et al. | |
| 5,333,622 A * | 8/1994 | Casali et al. | 128/864 |
| 5,409,460 A * | 4/1995 | Krumme | 604/107 |
| 5,483,027 A * | 1/1996 | Krause | 181/135 |
| 5,827,268 A * | 10/1998 | Laufer | 606/28 |
| 5,921,935 A * | 7/1999 | Hickey | 600/485 |
| 6,094,494 A * | 7/2000 | Haroldson | 381/328 |
| 6,251,093 B1 * | 6/2001 | Valley et al. | 604/97.03 |
| 6,256,396 B1 | 7/2001 | Cushman | |
| 6,339,648 B1 | 1/2002 | McIntosh et al. | |

(Continued)

OTHER PUBLICATIONS

Office Action for U.S. Appl. No. 12/492,164, filed Jun. 26, 2009, mailed Jan. 18, 2012.

(Continued)

*Primary Examiner* — David Warren
*Assistant Examiner* — Christina Russell
(74) *Attorney, Agent, or Firm* — RatnerPrestia

(57) ABSTRACT

Methods and devices for sound isolation are provided. A sound isolation device includes an expandable element and an insertion element. The expandable element is operatively attached to the insertion element. The expandable element includes an expanding medium, where the pressure of the expanding medium is varied to vary a sound isolation across the expandable element.

13 Claims, 10 Drawing Sheets

(56) References Cited

U.S. PATENT DOCUMENTS

| | | |
|---|---|---|
| 6,393,130 B1 | 5/2002 | Stonikas et al. |
| 6,671,381 B1 | 12/2003 | Lux-Wellenhof |
| 7,130,437 B2 | 10/2006 | Stonikas et al. |
| 7,164,775 B2 | 1/2007 | Meyer et al. |
| 7,215,789 B2 * | 5/2007 | Shennib et al. ............... 381/328 |
| 7,227,968 B2 * | 6/2007 | van Halteren et al. ........ 381/328 |
| 7,362,875 B2 * | 4/2008 | Saxton et al. ................. 381/322 |
| 7,387,187 B2 | 6/2008 | Widmer et al. |
| 7,424,123 B2 * | 9/2008 | Shennib et al. ............... 381/328 |
| 7,664,282 B2 * | 2/2010 | Urso et al. .................... 381/328 |
| 8,312,960 B2 * | 11/2012 | Keady ............................ 181/135 |
| 2004/0215053 A1 * | 10/2004 | Jorgensen et al. .............. 600/25 |
| 2006/0159298 A1 * | 7/2006 | von Dombrowski et al. . 381/330 |
| 2007/0116319 A1 | 5/2007 | Hagberg |
| 2007/0183613 A1 * | 8/2007 | Juneau et al. ................. 381/322 |
| 2008/0144871 A1 | 6/2008 | Purcell et al. |
| 2009/0173353 A1 | 7/2009 | Purcell et al. |
| 2009/0214072 A1 * | 8/2009 | Staab et al. .................... 381/380 |
| 2009/0245530 A1 * | 10/2009 | Keady ............................ 381/72 |
| 2009/0320858 A1 | 12/2009 | Purcell et al. |
| 2009/0320859 A1 | 12/2009 | Purcell et al. |

OTHER PUBLICATIONS

Office Action for U.S. Appl. No. 12/492,164, filed Jun. 26, 2009, mailed Jul. 21, 2011.

Office Action for U.S. Appl. No. 12/492,164, filed Jun. 26, 2009, mailed Oct. 28, 2010.

* cited by examiner

| AUTHOR MODE OF OCCLUSION | 250Hz | | 500Hz | | 1000Hz | | 2000Hz | |
|---|---|---|---|---|---|---|---|---|
| | OCCLUSION | | OCCLUSION | | OCCLUSION | | OCCLUSION | |
| | SHIFT | SD | SHIFT | SD | SHIFT | SD | SHIFT | SD |
| ELPERN & NAUNTON (TDH 39 MX41/AR) | | | 20 | 4 | 9 | 4.5 | 0 | 4.5 |
| GOLDSTEIN & HAYES (1965) (TDH 39 MX41/AR - MASTOLD) | | | 12.57 | 9.65 | 5.71 | 7.05 | 1.07 | 3.83 |
| GOLDSTEIN & HAYES (1965) (TDH 39 MX41/AR - FOREHEAD) | | | 13.11 | 6.58 | 4.86 | 3.52 | 0.43 | 2.99 |
| DIRKS & SWINDEMAN (TDH 39 MX41/AR) | | | 20.2 | 5.1 | 8.8 | 4.5 | .5 | 2.9 |
| HODGSON & TILLMAN** (TDH 39 MX41/AR) | | | 23.0 | * | 10 | * | -1 | * |
| FELDMAN, GRIMES & SHUR (TDH 39 MX41/AR) | | | 23.0 | 7.4 | 8.1 | 3.6 | -.1 | 6.9 |

| AUTHOR MODE OF OCCLUSION | 250Hz OCCLUSION | | 500Hz OCCLUSION | | 1000Hz OCCLUSION | | 2000Hz OCCLUSION | |
|---|---|---|---|---|---|---|---|---|
| | SHIFT | SD | SHIFT | SD | SHIFT | SD | SHIFT | SD |
| HUIZING (1960) - MASTOID (PLUG: DRUM & 1/4 WAVE BACK) | | | 15 | * | 8 | * | 1 | * |
| TYSZKA & GOLDSTEIN (EARMOLD - DEPTH NOT NOTED) | | | 9.5 | * | 11.2 | * | * | * |
| WIMMER (1986) (EARMOLD - STD. DEPTH) | 22 | | | | 17 | | 9 | |

1010 Electrodes

1010 Electrodes

1020 Spacer

1000C

OCCLUSION EFFECT MITIGATION AND SOUND ISOLATION DEVICE FOR ORIFICE INSERTED SYSTEMS

CROSS-REFERENCE TO RELATED APPLICATIONS

This application is a continuation of U.S. application Ser. No. 12/492,164, filed Jun. 26, 2009 which claims the benefit of U.S. provisional patent application No. 61/076,122 filed on 26 Jun. 2008. The disclosure of which is incorporated herein by reference in its entirety.

FIELD OF THE INVENTION

The present invention relates to devices that can be inserted into orifices and sealed, and more particularly although not exclusively related to earpieces with expandable systems.

BACKGROUND OF THE INVENTION

The occlusion effect is generally described as the sensation of increased loudness (sound pressure level), especially in the low frequencies, that a person experiences to self-generated sounds (vocalization, chewing, swallowing, walking, and the like), when the ears are covered (occluded). Note that this resonance amplification can occur in tubes that have a sealed volume and have acoustic leakage into the volume. The occlusion effect has been identified as a major obstacle to successful hearing aid use and shallow (within the first ½ of the channel) inserted earpieces. The theories of why the occlusion effect forms and what it is are numerous and diverse and to date no single explanation has been totally accepted.

FIG. 3 illustrates typical occlusion effect levels as a function of frequency for various in-ear devices.

There are several theories of the occlusion effect. They include outflow theory (Mach, 1863): occlusion of the ear canal results in an increase in middle ear impedance, and hence to a decrease in energy lost from the inner ear via the ossiculaer chain. Resonance theory (Huizing, 1923): increased perception of sound is brought about by the walls of this artificially closed cavity acting as resonators. Masking theory (Pohlman, 1930; Hallpike, 1930): occlusion of the ear canal eliminates masking influence of ambient noise. Inertial/osseotympanic theory (von Bekesy, 1932): the occlusion effect results from sound pressure increase in the auditory canal with occlusion. Inertia of the mandible to the skull sets up pressure variations in EAM. Impedance theory (Huizing, 1960): occlusion alters the impedance of the column of air in the canal (increasing it), resulting in improved coupling of the air in the canal to the middle ear.

FIG. 4 illustrates several occlusion effect studies and their values at various frequencies for earphones, while FIG. 5 illustrates several occlusion effect studies for earmolds. Roughly the occlusion effect is in the range of 13-25 dB between 250-500 Hz. Roughly from Killion, Wilber, and Gudmundsen (1988) a shallow insertion has an occlusion effect of about 13 to 21 dB, while a deep insertion has an occlusion effect of about 20 dB for a tapered tip, and about −9 to 4 dB for a bony contact ear inserted device. Related art solutions involve acoustic vents between the sealed region (now unsealed) and the outside environment of about 3 mm in diameter, however venting has limitations as well, for example ringing. Another solution is deep insertion with contact in the bony section of the ear canal.

Thus for shallowly inserted systems (e.g., <½ the ear canal length), the occlusion effect can be an issue (e.g., >5 dB).

SUMMARY OF THE INVENTION

At least one exemplary embodiment is directed to an occlusion effect mitigation device comprising: an insertion element; and an expandable element operatively attached to the insertion element, where the expandable element is configured to expand against a portion of the walls of a flexible channel forming a sealed chamber in the channel, where the expansion reduces the occlusion effect in the sealed chamber.

At least one exemplary embodiment is directed to a sound isolation device comprising: an expandable element; and an insertion element, where the expandable element is operatively attached to the insertion element, where the expandable element includes an expanding medium, where the pressure of the expanding medium is varied to vary sound isolation across the expandable element.

At least one exemplary embodiment is directed to a method of sound isolation comprising: expanding an element to a first pressure where the expanded element varies the sound isolation across the element as the pressure exerted by the expanding element is varied.

At least one exemplary embodiment is directed to a method of occlusion effect reduction comprising: inserting an insertion element into a flexible channel; and expanding an expanding element, where upon insertion of the insertion element and expansion of the expanding element a sealed chamber is formed, where when the expanding element presses against a portion of a wall of the flexible channel, the occlusion effect in the sealed chamber is reduced.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS OF THE PRESENT INVENTION

Figure 1:
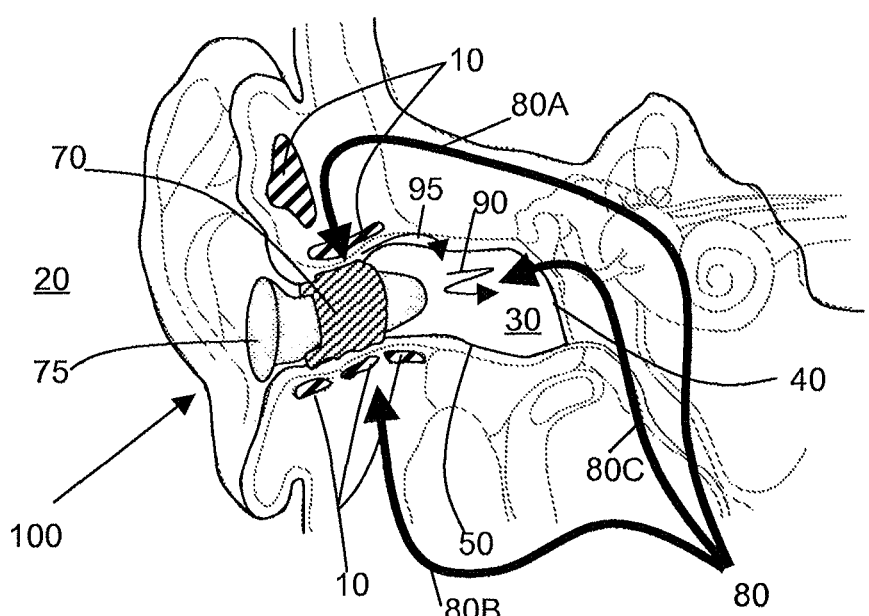
FIG. 1 illustrates an ear canal as a non-limiting example of an orifice that can be sealed forming a resonance chamber.

The following description of exemplary embodiment(s) is merely illustrative in nature and is in no way intended to limit the invention, its application, or uses.

At least several exemplary embodiments are directed to or can be operatively used on various wired or wireless earpiece devices (e.g., earbuds, headphones, ear terminal, hearing aids, behind the ear devices, or other acoustic devices as known by one of ordinary skill in the art, and equivalents).

Processes, techniques, apparatus, and materials as known by one of ordinary skill in the art may not be discussed in detail but are intended to be part of the enabling description where appropriate. For example material fabrication may not be disclosed, nor attachment procedures (e.g., adhesive attaching of separate ridge structures), but such, as known by one of ordinary skill in such arts is intended to be included in the discussion herein when necessary.

Notice that similar reference numerals and letters refer to similar items in the following figures, and thus once an item is defined in one figure, it may not be discussed or further defined in the following figures.

FIG. 1 illustrates a sealed (occluded) ear canal 50, with a sealed volume 30. Voice can leak 80 into the sealed volume 30 from various source paths 80A, 80B, and 80C. Source paths 80A and 80B represent sound conducted from bones 10 adjacent to ear canal 50. Source path 80C represents sounds 90, 95 to ear canal 50 from areas of the inner ear. In one explanation, the leaked acoustic energy results in an amplification (e.g., by resonance) at certain frequencies within the sealed volume, resulting in the occlusion effect. If the ear canal (a non-limiting example of an orifice) was unsealed then no resonance could build and hence there would be no occlusion effect. While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example exemplary embodiments do not require the formation of a sealed chamber in the channel, exemplary embodiments can increase the sound isolation across the sealed section of the channel.

FIG. 1 illustrates at least one exemplary embodiment. An earpiece 100 can include an insertion element 75 operatively connected to a sealing section. The sealing section can include an expandable element 70 (e.g., expanding polymers, inflatable systems, mechanically expanded systems, balloons of various shapes, sizes and materials, for example constant volume balloons (low elasticity <=50% elongation under pressure or stress) and variable volume (high elastic >50% elongation under pressure or stress) balloons). Many materials can be used for the expandable element 70. For example if the interior medium is air then the material (e.g., membrane) for the expandable element can be chosen so that the pressurized air (e.g., 0.1 bar gauge to 2 bar gauge) leaks through the membrane in a chosen period of time (e.g., 5% pressure decrease in 8 hours). Additionally other fluids (e.g., air, water, oil, glycerin) can be used as the interior medium. A pumping mechanism can be used to pressurize the interior medium. For example a manual pump, electrical pumps, and chemical pumps (e.g., electrolysis). Sealed volume 30 is formed between expandable element 70 and tympanic membrane 40. Expandable element 70 may seal ear canal 50 from sound in ambient environment 20 external to ear canal 50.

Figure 2:
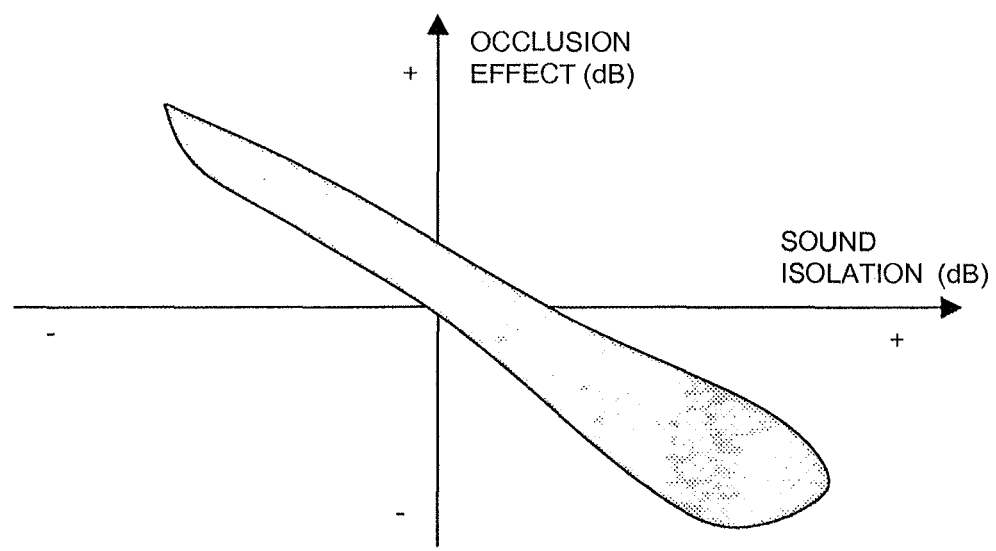
FIG. 2 illustrates occlusion effect values of at least one exemplary embodiment when the device is sealed at various sound isolation values.
Figures 3, 4:
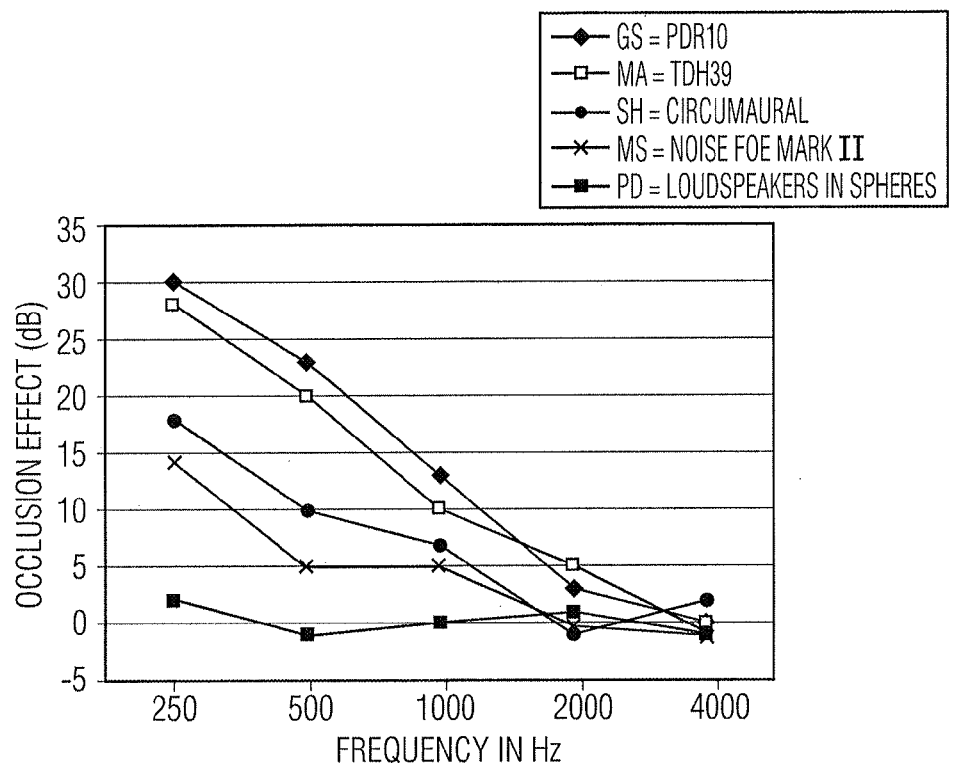
FIGS. 3-5 illustrates various values of the occlusion effect according to several scientific studies.

FIG. 2 is a graph of the occlusion effect as a function of sound isolation in accordance with an exemplary earpiece of the present invention. The example illustrates occlusion effect values when an exemplary earpiece is sealed at various sound isolation values. FIG. 2 shows that the occlusion effect is reduced as sound isolation is increased. Conversely, the occlusion effect increases as the sound isolation decreases.

Figures 5, 6:
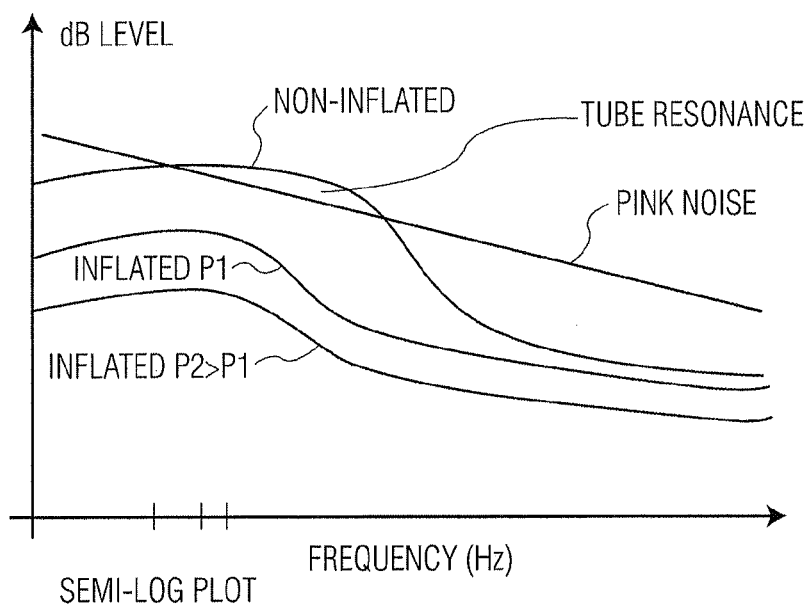
FIG. 6 illustrates sound isolation values (e.g., acoustic energy absorption and reflection) for an inflatable system according to at least one exemplary embodiment.

FIG. 6 illustrates sound isolation (attenuation+reflection) results as a function of inflation plotted in semi-log scale. Note that the inflation can be varied to obtain a variation in the attenuation and/or acoustic reflection. Additionally the inflation medium (interior medium) can be either a liquid (e.g., water, baby oil, mineral oil), a gas (e.g., H2O vapor, H2, O2 gas), or a combination of both. Thus in accordance with at least one exemplary embodiment sound isolation can be increased as the pressure is increased above a particular seal pressure value. However if the expandable element is a stressed membrane, then there can be an elongation percentage where the acoustic transmission through the membrane is higher than at larger or lower elongation percentage. For example if the stressed membrane is stretched to 50% elongation in one dimension the acoustic transmission can be lower than unstretched or 150% elongation stretched (stressed) membranes. The seal pressure value is the pressure at which the inflatable system (an example of an expandable element) has conformed to the inside of the orifice (e.g., whether regular or irregular) such that a drop between the sound pressure level on one side of the inflatable system is different from the sound pressure level on the opposite side of the inflatable system by a drop value in a short period of time. For example when a sudden (e.g., 1 second) drop (e.g., 3 dB) occurs at a particular seal pressure level (e.g., 2 bar). For example if a balloon is used where the medium is air, an internal pressure of 1.2 bar absolute (0.2 bar gauge) can result in a sound isolation of 20+ dB across the balloon. For permeability consideration, for example suppose one wishes inflation to last for 8 hours with less than 5% internal loss of pressure, the permeability will have to be much better than silicon, for example Teflon. For variable volume balloons (such as silicon balloons) various high elongation materials (some over 1000%) can have the requisite permeability.

Figure 7:
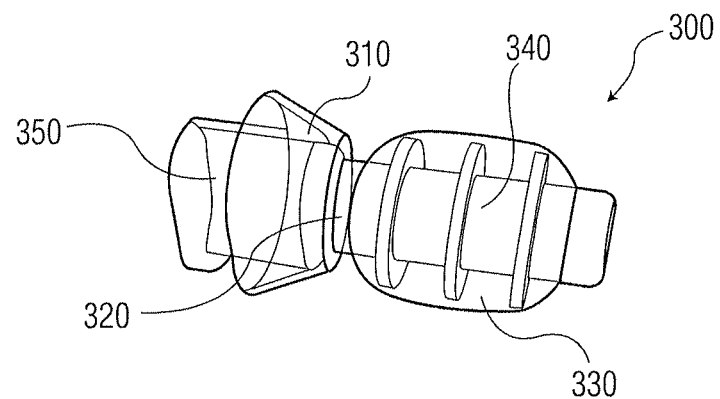
FIG. 7 illustrates an inflatable device in accordance with at least one exemplary embodiment.

FIG. 7 illustrates an inflatable system 300 comprising an insertion element (e.g., 320, multi-lumen tube) and an expandable element (e.g., 330, urethane balloon, nylon balloon). The expandable element can be filled with an expanding medium (e.g., gas, liquid, electroactive polymer or gel) fed via a supply tube (e.g., 340). The device illustrated in FIG. 7 illustrates a flange 310 (e.g., made of plastic, foam, rubber) designed to stop at a designated position in the orifice (e.g., at the opening of the orifice), and an instrument package (e.g., 350) can include additional devices and equipment to support expansion control (e.g., power supply and leads, gas and/or fluid generation systems).

Figure 8:
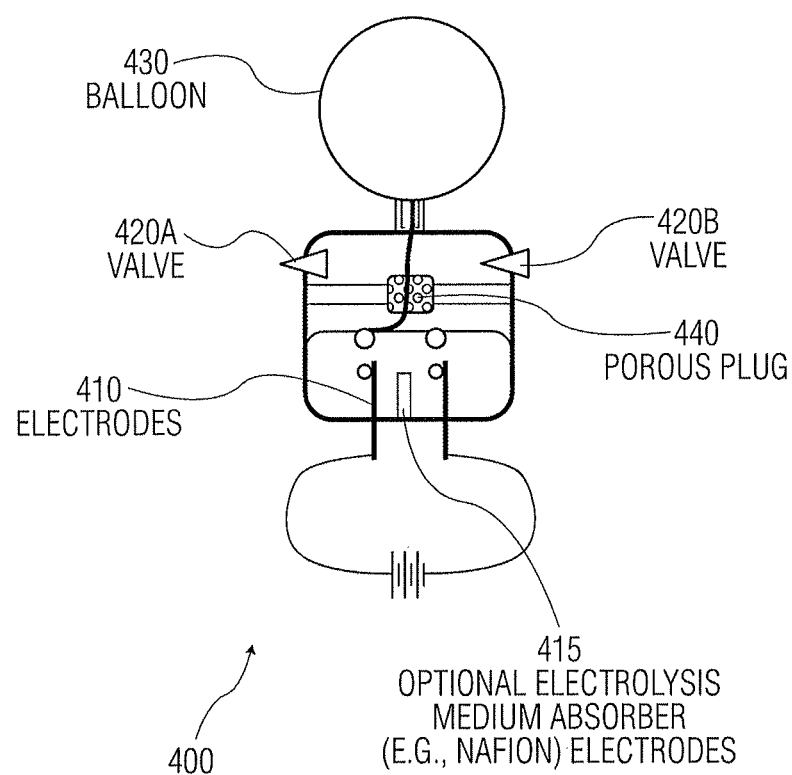
FIGS. 8-13, and 15 illustrate at least one method of inflating an inflatable device in accordance with at least one exemplary embodiment.

FIG. 8 illustrates at least one exemplary embodiment for pressure generation and control, designated generally as system 400. The non-limiting example illustrated includes a balloon (e.g., 430), at least one pressure control valve (e.g., 420A, 420B); electrodes 410, a porous plug (e.g. 440, micro pore plastics that allow gas to pass but block fluid motion), and optionally a membrane (e.g., 415, Nafion™) that absorbs the electrolysis medium (e.g., H2O with NaCl dissolved at 0.001 mole/liter) allowing a current to pass between the electrodes as if the electrodes were essentially in free electrolysis material, and at the same time preventing the electrodes from touching. The membrane facilitates close placement of the electrodes increasing the electric field and hence the current. As illustrated the seal pressure value is as discussed above, the operating pressure is some value greater than the seal pressure value (e.g., 20% greater) at which an expandable element operates for a given condition. FIG. 8 illustrates an electrolysis system where the gas generated passes through a porous plug into a chamber that has control valves. The control valves are designed to allow a certain gauge pressure value to be reached inside the chamber (e.g., 0.25 bar, 0.5 bar gauge) while allowing gas from the outside of the chamber to enter if the gauge pressure value drops below a value (e.g., −0.5 bar gauge), where the gauge pressure in this instance is calculated as the pressure inside the chamber minus the pressure outside the chamber. A non-limiting example of sealing time is 12 seconds for a balloon volume of 1000 mm^3 using <12 volts and less than 300 milliamps.

An example of electrolysis conversion efficiency is conversion at 75% efficient, roughly 4.0 J/per inflation, or roughly 0.0002823 grams H2O for roughly 0.2823 mm^3 H2O.

Figure 9:
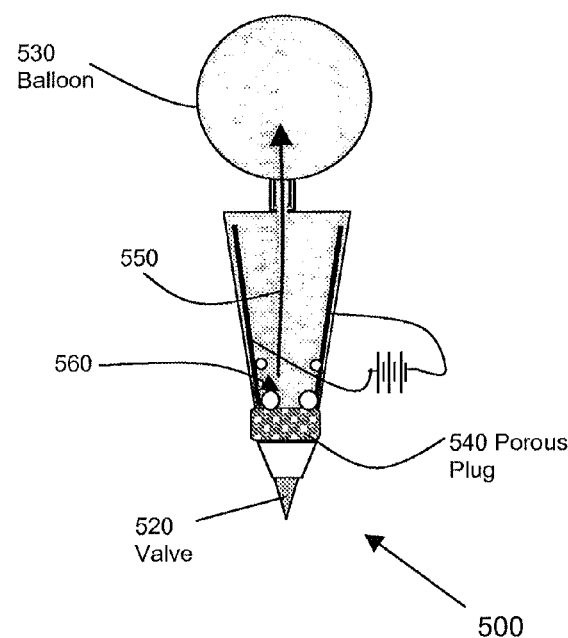

FIG. 9 is another exemplary embodiment of a pressure generation and management system 500 in accordance with at least one exemplary embodiment. In this exemplary embodiment the gas formation is controlled by controlling the size of the electric field (e.g., by relative placement of the electrodes (e.g., platinum cylinders)). As the gas is generated fluid must be displaced and a partially filled balloon 530 can start to fill. Near the gas formation region a porous plug 540 can be used to let the gas generated pass and a valve 520 (e.g., duckbill, for example from VERNAY™ or a MINI-VALVE™), or other types of valves, such as flapper valves, umbrella valves, spring and ball valves, and any other valves that have low leak rates (loss of less than 5% internal pressure in 8-16 hours), can be used to control the amount of pressure generated. Note that the fluid moves 550 by being displaced by controlling where the bubble formation 560 occurs (e.g., by placing the electrodes closer at the first desired bubble formation point).

Figure 10:
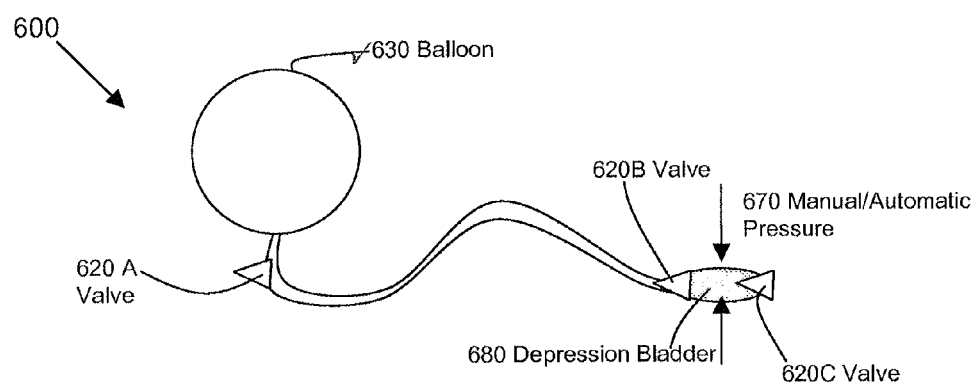

FIG. 10 illustrates another pressure generation and management system 600, which includes a manual depression bladder (e.g., 680). When depressed 670 the gas and/or fluid in the volume defined by the depression bladder (e.g., 680) can be encouraged (e.g., by correctly placed one-way valves (e.g., 620B, 620C)) to move the evacuated gas and/or fluid along a tube to further inflate or pressurize an expandable element (e.g., 630 Balloon). Another valve (e.g., 620A) can control the largest value of the pressure.

Figure 11:
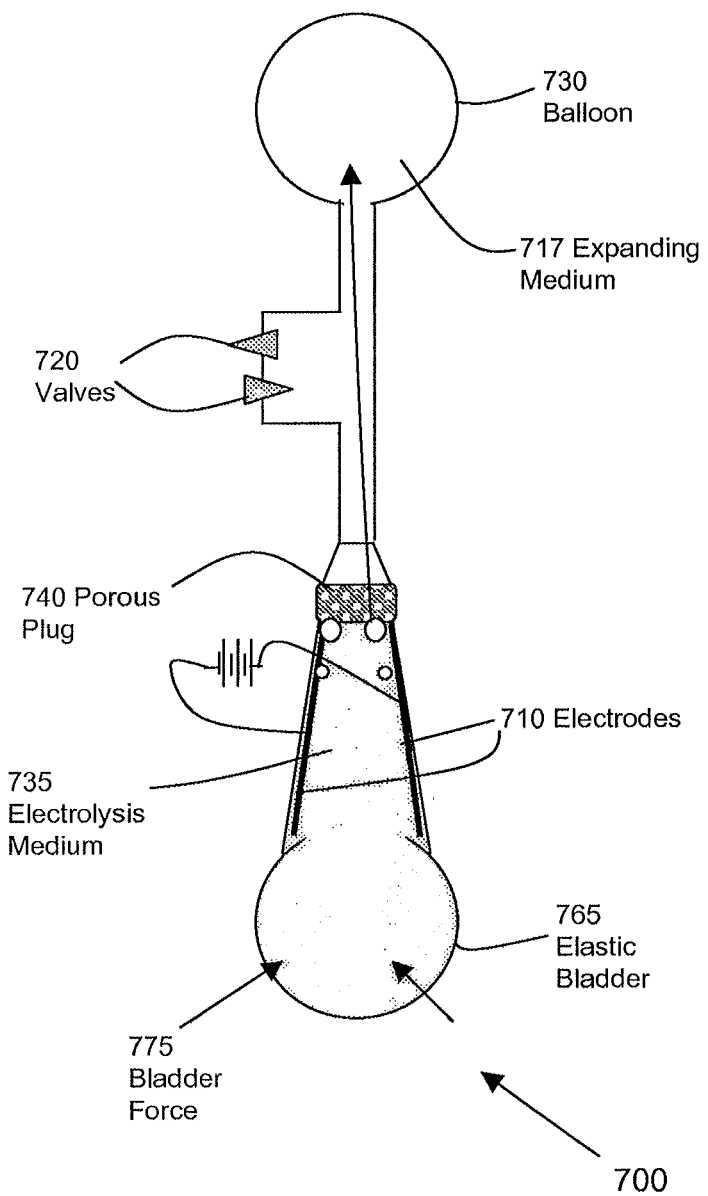

FIG. 11 illustrates another non-limiting example of a pressure generation and management system 700. System 700 includes electrolysis medium 735 and electrodes 710 for generating a gas via electrolysis. In the illustrated system 700 an elastic bladder (e.g., 765) provides a bladder force 775 that can aid in forcing any formed gas through the porous plug 740. The gas can be moved along a tube to fill balloon 730 with expanding medium 717. Valves 720 can control the pressure of expanding medium 717 to balloon 730.

Figure 12:
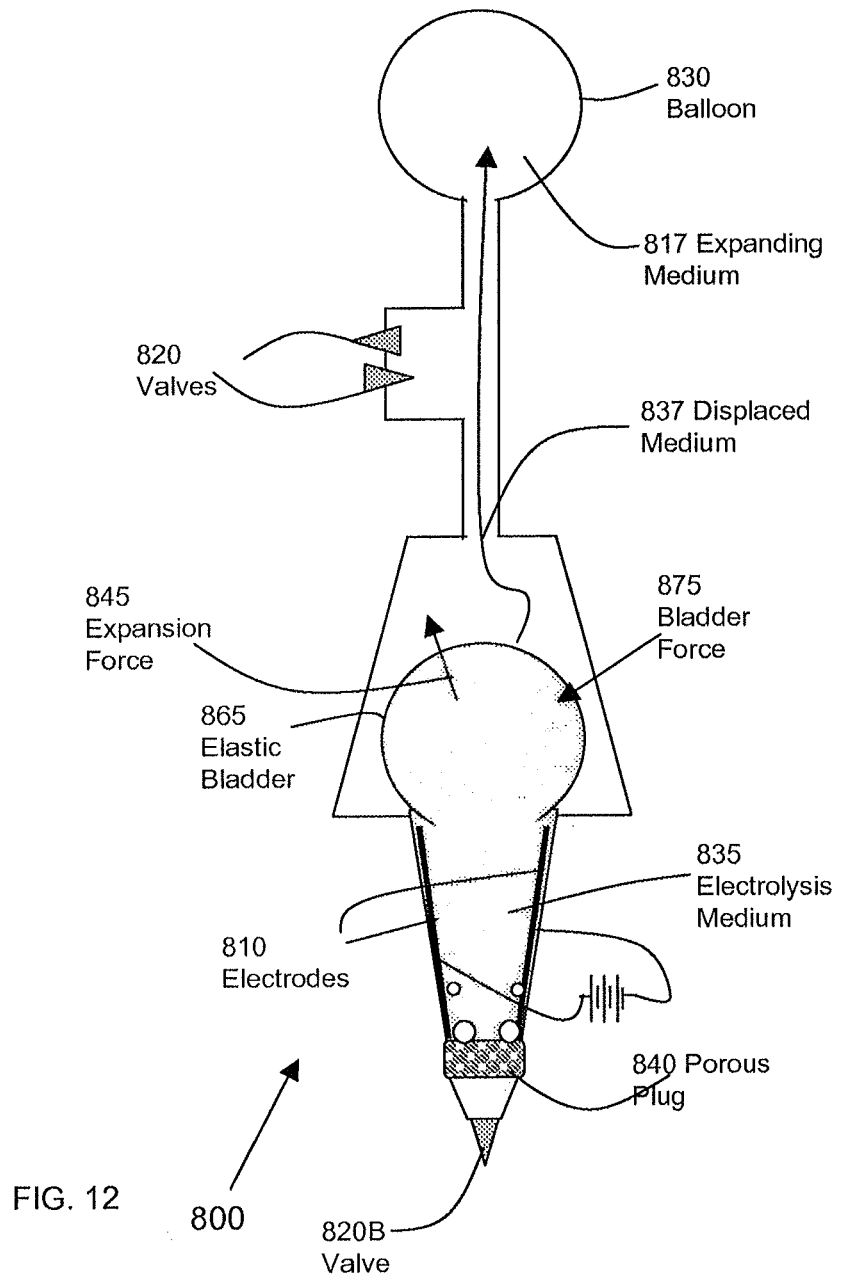

FIG. 12 illustrates yet another exemplary embodiment of a pressure generation and management system 800. In the system illustrated as gas is formed (via electrolysis medium 835 and electrodes 810), water is displaced expanding the elastic bladder 865 with expansion force 845. The expanding elastic bladder (e.g., compliant urethane) produces bladder force 875, displacing a medium (e.g., 837) in a chamber, where the displaced medium can further inflate an expanding element (e.g., Balloon 830) via expanding medium 817. Similar to system 500 (FIG. 9), system 800 includes porous plug 840 and valve 820B for controlling passage of the generated gas. System 800 may also include valves 820 for controlling the pressure to balloon 830.

Figure 13:
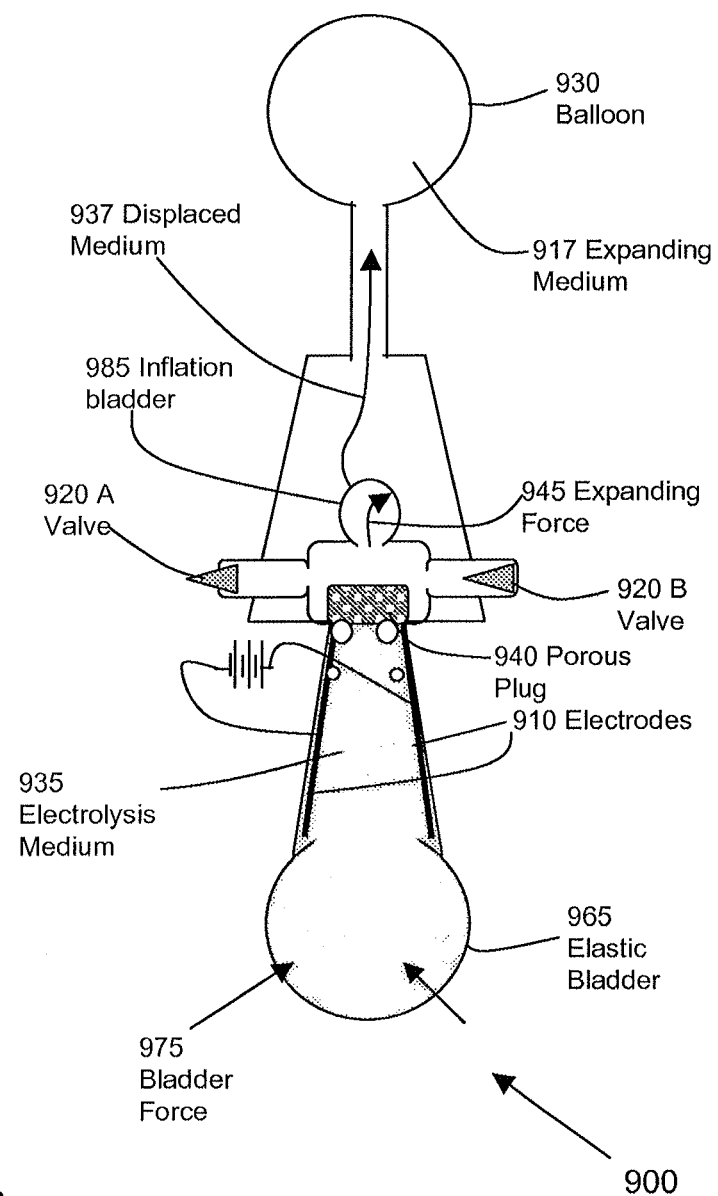

FIG. 13 illustrates yet another pressure generation and management system 900 according to at least one exemplary embodiment. System 900, similar to system 800 (FIG. 12), includes electrolysis medium 935, electrodes 910, and elastic bladder 965 which has a bladder force 975. As in FIG. 12 the gas is forced through the porous plug (e.g., 940), however in the configuration illustrated a smaller chamber is constructed with its own inflation bladder (e.g., 985) and the pressure control system (e.g., valves 920A and 920B) are operatively connected to the smaller chamber. Inflation bladder 985 produces expanding force 945, which displaces a medium (e.g., 937). Displaced medium 937 can inflate balloon 930, via expanding medium 917.

Figure 14A:
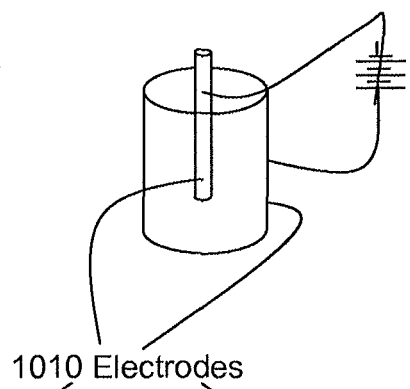
FIGS. 14A, 14B, and 14C illustrate various non-limiting examples of electrode configurations in accordance with at least one exemplary embodiment.
Figure 14B:
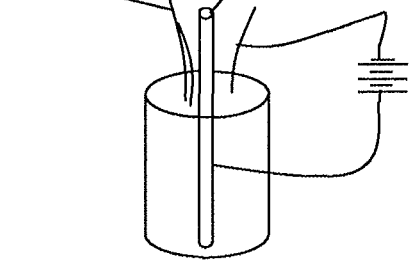
Figure 14C:
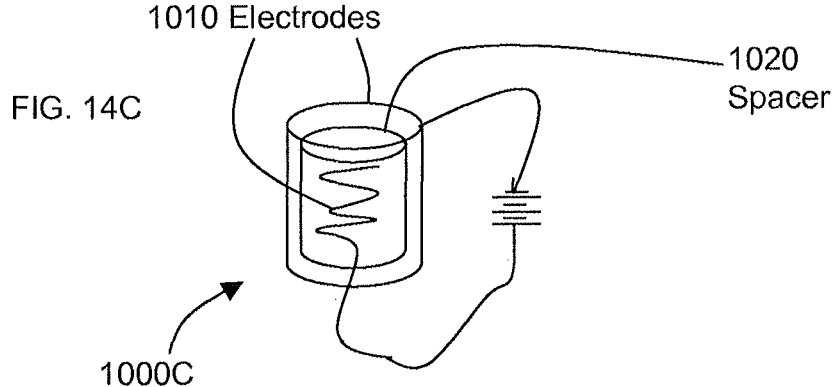

Although not mentioned to this point, the electrodes can vary in shape and relative size. For example the electrode producing more gas (e.g., the electrode associated with H formation in water) can be made large in surface area facilitating a greater formation area. Additionally the electrodes can be separated by an electrolysis medium absorber (e.g., Nafion™, 1020). FIGS. 14A through 14C illustrate several non-limiting arrangements of electrodes 1010. Note that the electrode material can vary, for example, the electrode may include a conductive material that will not oxidize in the electrolysis medium (e.g., stainless steel, platinum, gold). In FIG. 14C, electrolysis system 1000C includes spacer 1020 that allows current to flow between electrodes at a level similar to the current without the spacer but separates the electrodes so there is no shorting (e.g., Nafion™). This configuration can also keep air in but not water.

Figure 15:
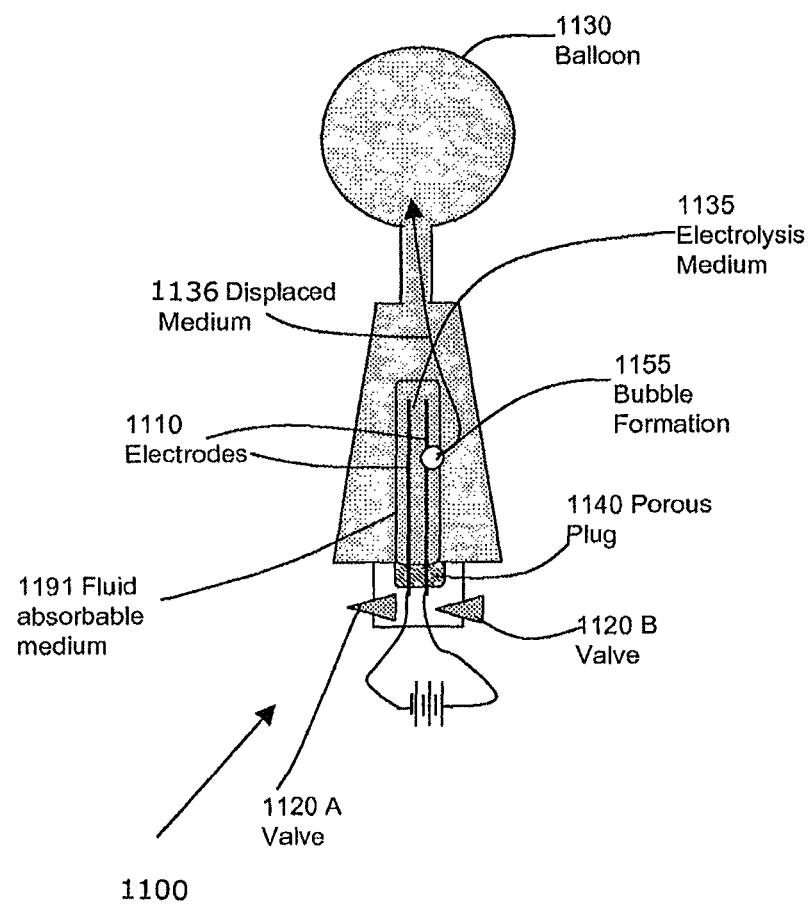

FIG. 15 illustrates at least one pressure generation and management system 1100 in accordance with at least one exemplary embodiment. In this system the electrodes 1110 are surrounded by a water soluble (porous) membrane 1191 (e.g., Nafion™), so that when gas is produced water is forced through the membrane 1191 while gas is still trapped inside the enclosed membrane chamber. An opening connected to a porous plug 1140 can allow the gas trapped to escape, and the pressure can be controlled by placing valves 1120A, 1120B after the porous plug 1140. Note that the electrodes 1110 can be positioned relative to each other to control the gas formation 1155 in electrolysis medium 1135. Displaced medium 1136 may be used to inflate balloon 1130.

Note that several configurations illustrate gas as the expanding and/or displaced medium. Note that other exemplary embodiments can use the same configuration for liquids. For example the displaced medium (e.g., 937) in FIG. 13 could be a fluid (gas or liquid).

At least one exemplary embodiment is directed to a device (e.g., an occlusion effect mitigation device, a sound isolation device, an earpiece) comprising: an insertion element (e.g., catheter, catheter with multiple interior channels, tube, body of an earpiece (thus possible irregular)); and an expandable element (e.g., stressed membrane, balloon, electroactive membrane, stressed foam or a combination of these) operatively attached to the insertion element, where the expandable element is configured to expand against a portion of the walls of a channel (e.g., an ear canal, nose, pipe) where the device is configured to seal the channel when expanded (e.g., inflated). Upon sealing the device can reduce sound transmission and/or the occlusion effect in any sealed chamber. Note that the catheter can have at least one interior channel and the interior channel can transmit acoustic energy. In at least one exemplary embodiment the expandable element is a balloon, with an expanding medium inside the balloon, where the expanding medium is at an operating pressure. The balloon can be variable volume (e.g., made of a material with an linear elongation >50% at operating pressure) or a constant volume balloon (e.g., a balloon made to a certain shape where upon inflation at an operating pressure does not expand more than 100% by volume from its shape volume). Note that the balloon shape can vary and be irregular or regular, for example disk shaped, conical, and/or spherical. Note that the operating pressure can be between 0.15 and 1 bar gauge pressure. Also note that the fluid can be ambient air.

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A device configured to be inserted in an ear canal, the device comprising:
   an expandable element including a partially inflated balloon and an expanding medium in the balloon, the expandable element configured to be expanded to a first operating pressure such that the expandable element conforms to a surface of the ear canal and such that, at the first operating pressure, the expandable element forms a chamber within the ear canal that is sealed from an outside environment; and
   an insertion element operatively attached to the expandable element,
   where the first operating pressure of the expanding medium is increased to a second operating pressure, to control an amount of sound isolation provided by the expandable element to the ear canal, thereby effecting an occlusion effect by the expandable element.

2. The device according to claim 1, where the insertion element is a catheter configured to transfer the expanding medium to the balloon.

3. The device according to claim 2, where the catheter has at least one interior channel.

4. The device according to claim 3 where the at least one interior channel is configured to transmit acoustic energy.

5. The device according to claim 2, where the catheter is coupled to a pressure generation system, the pressure generation system configured to provide the expanding medium to the expandable element via the catheter.

6. The device according to claim 5, where the pressure generation system includes at least one of an electrolysis pump, an electrical pump or a manual pump.

7. The device according to claim 1, where the balloon is at least one of disk shaped, conical or spherical.

8. The device according to claim 1, where the balloon is configured to include a linear elongation greater than 50% when inflated at the second operating pressure.

9. The device according to claim 8, where the second operating pressure is between 0.15 and 1 bar gauge pressure.

10. The device according to claim 9, where the expanding medium includes air.

11. A method for occluding an ear canal comprising:
    expanding a partially inflated balloon in the ear canal to a first operating pressure via an expanding medium in the balloon such that the balloon conforms to a surface of the ear canal and such that, at the first operating pressure, the balloon forms a chamber within the ear canal that is sealed from an outside environment; and
    increasing the first operating pressure of the expanding medium to a second operating pressure to control an amount of sound isolation provided by the balloon to the ear canal, thereby effecting an occlusion effect by the expandable element.

12. The method according to claim 11, where the balloon is configured to include a linear elongation greater than 50% when inflated at the second operating pressure.

13. The method according to claim 11, where the second operating pressure is between 0.15 and 1 bar gauge pressure.

* * * * *

UNITED STATES PATENT AND TRADEMARK OFFICE
CERTIFICATE OF CORRECTION

| | |
|---|---|
| PATENT NO. | : 8,522,916 B2 |
| APPLICATION NO. | : 13/653546 |
| DATED | : September 3, 2013 |
| INVENTOR(S) | : John P. Keady |

It is certified that error appears in the above-identified patent and that said Letters Patent is hereby corrected as shown below:

On the Title Page

Item (72) delete "Jon" and insert --John--

Signed and Sealed this
Nineteenth Day of March, 2024

Katherine Kelly Vidal
*Director of the United States Patent and Trademark Office*